United States Patent [19]  [11] 4,100,022
Ogasa et al.  [45] Jul. 11, 1978

[54] PROCESS FOR PREPARING A CURING AGENT FOR MYELOGENIC LEUKEMIA

[75] Inventors: Katsuhiro Ogasa, Yokohama; Morio Kuboyama, Tokyo; Minoru Saito, Komae; Kazuhiro Nagata, Tokyo, all of Japan

[73] Assignee: Morinaga Milk Industry Co., Ltd., Tokyo, Japan

[21] Appl. No.: 727,653

[22] Filed: Sep. 29, 1976

[30] Foreign Application Priority Data

Oct. 17, 1975 [JP] Japan ................................. 50-124435

[51] Int. Cl.² ............................................... C12K 9/00
[52] U.S. Cl. ..................................................... 195/1.8
[58] Field of Search ......................................... 195/1.8

[56] References Cited
PUBLICATIONS

Chem. Abst. Gen. Subj. Index–vol. 8.3 (1975) p. 98 G.S.

*Primary Examiner*—Sam Rosen
*Attorney, Agent, or Firm*—Oblon, Fisher, Spivak, McClelland & Maier

[57] ABSTRACT

A process for preparing a therapeutic agent characterized by preculturing human amnion cells isolated from human amnion by trypsinization or human amnion cells obtained by subculturing the isolated cells in a medium containing calf or bovine fetal serum at least one time for 1 to 5 days to form a monolayer, removing the medium, adding a medium containing 0.5 to 20 mg of human serum albumin per 1 ml of medium thereto and culturing it for 3 to 6 days, dialyzing the culture liquid against diluted buffer or water, and filtering the dialyzed culture liquid through a bacterial filter thereby obtaining a germ free liquid agent.

2 Claims, No Drawings

PROCESS FOR PREPARING A CURING AGENT FOR MYELOGENIC LEUKEMIA

BACKGROUND OF THE INVENTION

1. Field of the Invention

The present invention relates to a process for preparing a therapeutic agent having the effect of restoring normal functions against dis-differentiated myelogenic leukemic cells from a culture liquid obtained by culturing a human amnion cell individually isolated by trypsinization treatment of human amnion membrane or a human amnion cell obtained by subculturing the isolated cell in a medium containing calf or fetal bovine serum at least one time, in a medium containing human serum albumin.

Myelogenic leukemia is a disease characterized by wide spread proliferation of the myleoid cells and the precursor cells in the bone marrow. The therapeutic agent prepared according to the process of the present invention acts against leukemic cells produced by the disorder of bone marrow to restore the normal function of the cells.

2. Description of the Prior Art

Medical research for methods of treating leukemia has hitherto been directed to the development of techniques which counter the cytotoxic effects of leukemia cell. However, recently the restoration of normal functions against dis-differentiated leukemic cells, that is, the development of a medicinal agent which promotes the decarcinogenesis of cancer cells has ben pursued (Chemistry and Biology, Vol. 13, No. 6, pp 380 to 382, 1975). Ichikawa et al. have described a process for preparing a medicinal agent which includes decarcinogenesis in which mammal fetal cells are cultured (Journal of Cellular Physiology, 74, 223, 1969; 76, 175, 1970 and Gann, 64, 257, 1973). Another conventional method is the Sachs et al method (Proceedings of the National Academy of Sciences of the United States of America, 70, 343 1973).

The Ichikawa et al method is as follows:

The fetus of a mouse is exenterated aseptically and sliced aseptically by a pair of scissors, and then a buffer solution containing trypsin is added thereto to isolate the fetal cells. The isolated cells are placed on a plate and a medium is added thereto in which the cells are cultured whereby primary culture cells are obtained. A suitable culture medium is the Eagle MEM medium combined with 10% (V/V) horse or calf serum. The cells grow in the form of a monolayer and are peeled from the glass surface of the plate with trypsin and cultured in the same medium again to obtain a secondary culture of the cells. In either case culturing is conducted in a carbon dioxide culture vessel containing 5% carbon dioxide at a temperature of 37° C and a humidity of 100% for 3 to 5 days.

In the secondary culture liquid a substance which is capable of restoring normal functions against the dis-differentiated myelogenic leukemic cells of mouse to differentiated mature granulocytes or macrophages exists. The substance is known to be a non-dialysable high molecular protein which is inactivated by heating at 70° C for 30 minutes or by treatment with a solution containing trypsin in a concentration of 0.4 mg/ml at 37° C for 2 hours.

The Sachs et al. method is as follows:

The E1 cells which are established as a culture cell line from the fetus cells of a Swiss mouse are dispersed in an Eagle MEM medium combined with 10% of horse serum and placed in a plastic plate. After culturing the cells at 37° C for 3 to 4 days whereby a monolayer of cells is formed, the monolayer is removed from the medium and is washed with Dulbecco's phosphate buffered saline (hereinafter referred to as PBS$^\ominus$) 3 to 4 times. Thereafter, an Eagle MEM medium not containing serum is added thereto and the cells are further cultured at 37° C for 3 to 4 days. It is known that the culture liquid thus obtained contains a substance which is capable of restoring normal functions to dis-differentiated myelogenic leukemic cells of the mouse thereby differentiating to mature granulocytes or macrophages. The active substance is refined to an electrophoretically single protein by subjecting the culture liquid to ultrafiltration with a Diaflo membrane, Hydroxylapatite column chromatography, DEAE-Cellulose column chromatography and Sephadex G-150 column Chromatography in that order. It is known that this substance is a protein of about 68,000 in molecular weight and does not contain cystine, cystein, hexosamine and sugars and is inactivated by pronase treatment. However, these conventional methods have the following deficiencies:

As recognized by Dr. Ichikawa himself, the Ichikawa et al method has the deficiency that there is about four times the difference in the effect of a culture liquid for the restoration of normal functions against dis-differentiated leukemic cells depending upon the kinds of animal serum added to the growth medium and upon the lots of serum used even if the serum is derived from the same kind of animal. (Experimental Research, 90, 20, 1975) The Sachs et al. method is specific only to E1 cells established as a cultured cell line. It is apparent from further research on various cells established as a cultured cell line, that a substance which has the ability to restore normal functions to cells, as Dr. Sachs et al. insist is present, has not been identified as present in the culture liquid.

Recently, Dr. Maeda et al. have reported that a culture liquid containing a substance which has a normal restorative effect against dis-differentiated leukemic cells in a a high concentration is obtained by culturing animal fetus cells in a medium to which is added bovine serum albumin as a mammal serum in order to improve the conventional methods. (The 34th General Meeting of the Cancer Society of Japan, pp 127, 1975). Also, Dr. Ichikawa et al. have reported that a culture liquid having the same activity is obtained by culturing human fetus cells in a medium to which is added calf serum (Gann. 64, 3 247–263, 1973). However, these methods use cells of animals other than human beings or human fetus cells, sera or serum albumin of animals other than human beings. Therefore, when a medicinal agent derived from a culture liquid obtained by these methods is administered to a human being, an antigen-antibody reaction which originates from the serum or serum albumin of an animal other than a human being takes place so that the medicinal agent cannot be practically used. It is detrimental to public order or good morals to use human fetus cells. Thus, these conventional methods cannot be industrially employed.

As the result of investigating processes for preparing a therapeutic agent for myelogenic leukemia which does not induce an antigen-antibody reaction which is the most serious defect of the conventional methods, a culture liquid has been developed from cultured human amnion cells. These cells have never been used for preparing a therapeutic agent. The cells are easily available in media containing human serum albumin and have the effect of restoring normal functions to dis-differentiated myelogenic leukemic cells.

SUMMARY OF THE INVENTION

The present invention relates to a process for preparing a therapeutic agent characterized by preculturing human amnion cells isolated from human amnion by trypsinization or human amnion cells obtained by subculturing the isolated cells in a medium containing calf or bovine fetal serum at least one time for 1 to 5 days to form a monolayer, removing the medium, adding a medium containing 0.5 to 20 mg of human serum albumin per 1ml of medium thereto and culturing it for 3 to 6 days, dialyzing the culture liquid against diluted buffer or water and filtering the dialyzed culture liquid through a bacterial filter thereby obtaining a germ-free liquid agent.

DETAILED DESCRIPTION OF THE PREFERRED EMBODIMENTS

(1) Preparation of Amnion Cell

The amnion used in the present invention is selected from the placenta of a woman who has normally delivered a child or who has delivered by cesarean section. The amnion is immersed in a sterilized Hank's solution containing penicillin in a concentration of 0.3% (W/V) and preserved at 4° C until the preparation of therapeutic agent is commenced. Because the amnion which is employed is derived from a woman who has normally delivered a child, it is contaminated with an antiseptic solution which is used to sterilize the passage through which passes a baby in childbirth. Accordingly, the danger exists that the antiseptic can have an adverse influence upon the preparation of therapeutic agent. Therefore, it is desirable to use an amnion derived from the placenta of a woman who has delivered a child by cesarean section, if possible. The amnion which is severed from the placenta is desirably used for the preparation of a therapeutic agent as soon as possible after delivery. Even when the amnion is preserved at a low temperature, the amnion cells will die within 24 hours after delivery. The above described amnion is washed aseptically with sterilized PBS$^\ominus$ and a sterilized Eagle MEM medium (manufactured by Nissui Seiyaku Company) two times each, and is cut into about 5 cm square pieces which are placed into a plate, the pieces are washed three times with an Eagle MEM medium, sliced aseptically with scissors, added to an aqueous solution containing trypsin in a concentration of 0.25% by weight and stirred aseptically at room temperature for 30 to 60 minutes for the enzymatic reaction. A sterilized Eagle MEM medium containing 10 to 20% of calf or fetal bovine serum is added to the trypsin digested solution to prevent the action of trypsin and the mixture is passed through a stainless sieve of 80 to 150 mesh to aseptically remove cell masses.

(2) Primary Culture

The amnion cell suspension thus obtained is centrifuged aseptically at 1,000 r.p.m. for 10 minutes to collect the cells which are then suspended in the same sterilized Eagle MEM medium. A part of the suspension is withdrawn and its viable cell count is measured by the following Eosine dyeing method. The amnion cells are inoculated with a sterilized Eagle MEM medium within the range of $5 \times 10^6 \sim 10^7$ per each 10ml portion of medium. In the Eosine test, an eosine solution of eosine Y powder dissolved in PBS$^\ominus$ in a concentration of 0.5% (W/V) and the cell suspension are mixed in the same amounts. One drop of the mixture is dropped onto a haemacytometer and observed under a microscope. A viable cell count is measured by calculating the red dyed cells as dead cells and the non-dyed cells as living cells.

In the process of the present invention, the medium used for preculturing cells or forming a monolayer of cells is prepared by adding 10 to 20% of calf serum (within a week after birth) or fetal bovine serum to a medium (hereinafter referred to as EM medium) prepared by adding MEM amino acid vitamin medium (manufactured by Nissui Seiyaku Company) to Eagle MEM medium in such a manner that the amino acid and vitamin content is two times greater than the amount of Eagle MEM medium.

Although a plate may be employed for culturing the isolated amnion cells, a large cell culture vessel (manufactured by Sterilin Company) is desirably used for the purpose of preparing a large amount of therapeutic agent. This culture vessel is set up so that a plastic film in a spiral shape for the growth of adhering cells thereon can be inserted in the cylinder.

The human amnion cells isolated as described above are inoculated in a 10ml medium per plate and cultured in a carbon dioxide culture vessel at 37° C and 100% humidity. After 3 to 4 days, the medium is exchanged with a fresh medium to remove floating dead cells and erythrocytes. The cells are further cultured under the same conditions for several days until the cells adhere to the bottom surface of the plate to form a monolayer of cells thereon. Thus, a primary culture of cells is obtained. The primary culture cells can be used for preparing a therapeutic agent.

(3) Subculture

After the primary culture cells are obtained, the medium is removed and the cells are washed with PBS$^\ominus$ and are peeled from the bottom surface of the plate by adding 0.05% (by weight) of an aqueous trypsin solution thereto. A viable count of cells is determined in the same manner by the Eosine dyeing method and diluted with an EM medium to a concentration of $5 \times 10^5 \sim 10^6$ cells pern ml. The cell solution is then placed into a plastic plate together with ME medium to which is added calf or fetal bovine serum and cultured in the same manner to obtain a secondary culture of cells. The secondary cell culture can be used for preparing a therapeutic agent.

In the process of the present invention it is desirable to prepare a therapeutic agent using the secondary human amnion cells so subcultured at least one time by the conventional method. The subculture operations are performed in order to obtain amnion cells which do not contain unnecessary ingredients such as dead cells and erythrocytes. Furthermore, when the amount of secondary human amnion cells is so small that they cannot be cultured in large amounts, one or more subcultures are repeated to increase the number of cells and the tertiary and further cultured cells can be used for preparing a therapeutic agent. In such cases, the proliferation cells is gradually suppressed as the subcultures are repeated, and it has been found that a substance having the effect of restoring normal functions to dis-differentiated leukemic cells cannot be obtained from cells which change morphologically and which proliferate infinitely. Thus, the subculture is limited to 15 repetitions.

(4) Preculture

The human amnion cells isolated as described above or subcultured are inoculated with an EM medium to which is added the same serum as described above in a ratio of $5 \times 10^6 \sim 10^7$ cells per 10ml of medium and cultured in a carbon dioxide culture vessel at 37° C for 1 to 5 days so that the cells adhere on the bottom surface of the plate. Thereafter, the medium is removed and the cells are washed three times with PBS$^\ominus$ to completely remove serum and to finish the preculture. The preculture is performed so that the human amnion cells can adhere onto the bottom surface of the plate. However, it is not an objective to obtain a culture liquid. The period of preculture is determined by Test 1.

Test 1

The M1 cell line established by Ichikawa et al. from mouse bone marrow of SL mice having spontaneous myeloblastic leukemia in a line comprising myeloblastic leukemic cells which repeat proliferation in media in their indifferentiated state under ordinary culture conditions. However, if the M1 cells differentiate to granulocytes or macrophages having mobility and phagocytotic activity when a therapeutic agent, whose function is to restore the normal functions of myelogenic cells against leukemic cells, (M1 cell) is added to the medium and the cells are cultured, then, the therapeutic agent is deemed to be effective for myelogenic leukemia. The present inventors have examined the phagocytatic activity of M1 cells cultured in a medium containing the therapeutic substance according to the present invention and culture. Five kinds of samples were prepared in the same manner as described in Example 1 with the exception that the number of days of preculturing was varied from 0, 1, 3, 5, to 7.

The effect of the therapeutic agent on the phagocytotic activity was determined on these samples as follows:

A medium was prepared by adding 10% calf serum to the EM medium. Five ml samples of several test media were prepared by adding a portion of a liquid sample containing the therapeutic agent to the calf serum containing EM medium in a (V/V) ratio such that the concentration of therapeutic agent containing medium to calf serum containing medium was 25%. A control sample (Control 1) was prepared by not adding the therapeutic agent containing liquid to the calf serum containing EM medium. All samples including the control were inoculated with $5 \times 10^5$ M1 cells each and cultured in a plastic plate 6 cm in diameter in a carbon dioxide culture vessel at 37° C for 3 days. After culturing, the cells were collected by a rubber cleaner and the cell count in each medium was measured by the above described eosine dyeing method. After removing the medium by centrifuging, the cells collected from each sample were suspended separately in 2ml of EM medium which did not contain calf serum. An aqueous suspension of polystyrene latex particles $1\mu$ in diameter was added at the rate of 1 drop per 20ml of medium. After allowing the solution to stand at 37° C for 4 hours, the cells were washed with PBS$^\ominus$ to sufficiently wash particles not phagocytized by the cells and the particles which adhered on the surface of cells. Then, one drop of cell suspension was placed on a hemocytometer and then one drop of eosine solution was added thereto, and the total viable cell count and the number of cells which incorporated polystyrene latex particles were measured under a microscope. The percentage of the latter to the former was calculated whereby the phagocytotic activity of cells for determining the effect of therapeutic agent was obtained. The results are shown in Table 1.

TABLE 1

| Days of preculturing (days) | Phagocytotic activity (%) |
|---|---|
| 0 | 19.2 |
| 1 | 68.8 |
| 3 | 67.7 |
| 5 | 60.0 |
| 7 | 56.3 |
| Control 1 | 0.4 |

In the sample which was not precultured almost all of the cells did not adhere to the bottom surface of the plate, but were suspended in the culture liquid and were low in phagocytotic activity. On the other hand, in the sample which was precultured for more than 5 days and then further cultured in a medium containing serum albumin for 4 days, although a decrease in phagocytotic activity was hardly noticed, it was observed that the cells peeled from the bottom surface of plate and were in suspension and disintegrated. The intracellular components were eluted into the culture liquid and the sample was found to be inappropriate for preparing a therapeutic agent.

From the above test results, it is evident that 1 day is sufficient for preculturing but it is difficult to form the cell monolayer. Preculturing may be performed for 5 days.

(5) Culture

In the process of the present invention, an EM medium containing 0.5 to 20 mg of human serum albumin per 1ml of medium is added to human amnion cells whose preculturing has been terminated as described above to form a monolayer and the human amnion cells are cultured in a carbon dioxide culture vessel at 37° C for 2 to 6 days whereby a culture liquid is obtained. The amount of human serum albumin added to medium and the number of days of culturing were determined in Tests 2 and 3.

Test 2

Seven kinds of samples were prepared in the same manner as in Example 1 with the exception that the amount of human serum albumin added to the medium varied from 0mg (Control 2), 0.25mg, 0.5mg, 1mg, 5mg, 20mg to 40mg per 1ml of medium. The phagocytotic activity of M1 cells was measured on these samples by the same method described in Test 1 to examine the effect of the therapeutic agent as a function of the amount of serum albumin added.

Incidentally, a sample which did not contain the culture liquid was prepared in the same manner as Control 1 of Test 1 and was used as Control 1. The results are shown in Table 2.

TABLE 2

| Amount of human serum albumin (mg/ml) | Phagocytotic activity |
|---|---|
| Control 1 | 0.8 |
| 0 (Control 2) | 6.0 |
| 0.25 | 10.5 |
| 0.5 | 36.2 |
| 1.0 | 56.5 |
| 5.0 | 72.7 |
| 20.0 | 63.7 |

TABLE 2-continued

| Amount of human serum albumin (mg/ml) | Phagocytotic activity |
|---|---|
| 40.0 | 48.5 |

No phagocytotic actitivy was observed in Control 1 and the sample (Control 2) cultured without added serum albumin. The results also verify that a sample cultured with 0.25mg/ml of human serum albumin is low in phagocytotic activity. In a sample cultured with 40mg/ml of human serum albumin, the cells disintegrated and the intracellular components were eluted. Therefore, these samples are not desirable for the preparation of a therapeutic agent. Accordingly, in the process of the present invention, the appropriate amount of serum albumin which is added to the medium is 0.5 to 20mg per 1ml of medium.

Test 3

Six kinds of samples were prepared in the same manner as described in Example 1 with the exception that the amnion cells were cultured after preculturing for 1, 2, 3, 5, 6 and 8 days. the phagocytotic activity of the M1 cells was measured on these samples by the same method described in Test 1 to examine the effect of the therapeutic agent.

Incidentally, a sample which dit not contain added culture liquid was prepared in the same manner as Control 1 of Test 1 and was used as Control 1. The results are shown in Table 3.

TABLE 3

| Days of culturing (day) | Phagocytotic activity (%) |
|---|---|
| 1 | 9.6 |
| 2 | 42.1 |
| 3 | 67.3 |
| 5 | 66.8 |
| 6 | 69.4 |
| 8 | 63.6 |
| Control 1 | 0.6 |

The sample which was cultured for 1 day was low in phagocytotic activity. The sample which was obtained by culturing for 8 days was high in phagocytotic activity. However, the phenomenon of the development of a monolayer of human amnion cells which can be peeled from the bottom surface of plate was not observed. Moreover, the cells disintegrated. Therefore, it is not desirable to collect a culture liquid from the sample to prepare a therapeutic agent.

Accordingly, in the present invention, the appropriate days of culturing are 2 to 6 days and, in order to shorten the days of culturing, culturing for 3 days is particularly desirable.

(6) Dialysis and Filtration

In the process of the present invention, the culture liquid prepared as described above is dialyzed against PBS⊖ to remove the medium components and is filtered aseptically. The filtered material is aseptically placed in a container whereby it is used directly as a fluid therapeutic agent. The dialyzed culture medium obtained by dialyzing the culture liquid against diluted PBS⊖ can be filtered through a bacterial filter to obtain a germ-free liquid agent, and, if necessary, further aseptically lyophilizing the liquid thereby obtaining a powdery curing agent. Also, the culture liquid is ultra-filtered whereby a fraction having a protein of 30,000 to 100,000 molecular weight as the main ingredient is obtained. The fraction can be aseptically filtered and used as a curing agent as a liquid or as a lyophilized powdery therapeutic agent. The powdery curing agent can be appropriately dissolved in sterilized water, sterilized physiological saline solution, dextrose solution or the like and administered by injection. Also the liquid therapeutic agent can be injected as it is.

(7) Effective Amount

Test 4

A test was conducted as to whether or not mice suffer from myelogenic leukemia when M1 cells are transplanted to the mice, which have been treated with a therapeutic agent obtained according to the process of the present invention.

Three kinds of medium were prepared by adding the culture liquid obtained by the same method as described in Example 1 to an EM medium so that the concentration of culture liquid ranged from 6.25%, 12.5% and 25% (V/V) and a control EM sample was prepared ;to which was not added the culture liquid. The four kinds of medium were inoculated with M1 cells in the amount of $3 \times 10^5$ cells per 1ml of medium and cultured in a carbon dioxide vessel at 37° C for 3 days. After culturing, a part of the M1 cells was withdrawn to test for phagocytotic activity in the same manner as in Test 1. The remaining M1 cells were washed twice with PBS⊖ and the viable cell count was determined by the above described eosine dyeing method. The cells were suspended in PBS⊖ in amounts of $1 \times 10^5$, $1 \times 10^6$ and $1 \times 10^7$ per 1ml to prepare M1 cell suspensions.

Forty four 6-week-old SL mice were divided into 11 groups of 4 mice each and 0.1ml of the above M1 cell suspension was injected once into each mouse through its tail vein. Each mouse was bred for 1 month with water and feed (manufactured by Nippon Kurea Company) was given freely. Thereafter, the mice were anatomized to observe whether there was an outbreak of myelogenic leukemia as determined by the state of enlargement of the lymphatic node and spleen in order to test for the decarcinogenic effect of therapeutic agent on M1 cells. The results are shown in Table 4.

TABLE 4

| Ratio of culture liquid added to medium (%) | Phagocytotic activity | Number of cell transplant | Number of animals suffering from leukemia Total numer of animals |
|---|---|---|---|
| 0 (Control) | 0.4 | $10^6$ | 4/4 |
| | | $10^5$ | 4/4 |
| | | $10^4$ | 2/4 |
| 6.25 | 18.2 | $10^6$ | 4/4 |
| | | $10^5$ | 2/4 |
| | | $10^4$ | 0/4 |
| 12.5 | 39.4 | $10^6$ | 1/4 |
| | | $10^5$ | 0/4 |
| | | $10^4$ | 0/4 |
| 25.0 | 68.1 | $10^6$ | 1/4 |
| | | $10^5$ | 0/4 |

As can be recognized from Table 4, the number of animals suffering from leukemia decreases as a function of an increase in the concentration of the therapeutic agent added to the M1 cell culturing medium. Moreover, particularly when the culture liquid was added in a concentration of above 12.5%, the number of animals suffering from the disease substantially decreased in comparison to the control. This shows that the functions of the M1 cells have been restored to normal by culturing the M1 cells in a medium which contains the therapeutic agent in a concentration of about 12.5%.

For the purpose of studying the effect when the therapeutic agent was injected into SL mice suffering from myelogenic leukemia by previously transplanting M1 cells thereto, the following animal experiment was conducted. The therapeutic agent obtained by the process of the present invention contains high molecular proteins and, therefore, when injecting the therapeutic agent into an animal, an antigen-antibody reaction takes place so that the curing agent cannot be administered repeatedly and thus the effect cannot be tested. Accordingly, the present inventors have prepared a therapeutic agent for animal experiments using cells and serum albumin from the same kind of animal used in the experiment in the same manner as in the present invention and tested therewith. That is, a therapeutic agent for an experiment is prepared by culturing mouse fetal cells in a medium to which is added mouse serum albumin and then is injected into a mouse to examine the extent of acute toxicity and the effective amount to be administered.

Test 5

26 Fetuses were exenterated aseptically from 3 SL mice in the 14th day of pregnancy, and were sliced aseptically by a pair of scissors. Then 60ml of an aqueous solution of trypsin in a concentration of 0.25% (W/V) were added thereto and the tissue was treated enzymatically at 37° C for about 15 minutes to isolate the fetus cells. The fetus cells in a concentration of $2 \times 10^6$ were inoculated into 30 plastic plates each 10cm in diameter containing 10ml of sterilized EM medium to which had been added 10% calf serum (manufactured by MBL Company, Lot No. 5340), and cultured in a carbon dioxide culture vessel for 6 days. The medium was replaced every other day whereby a monolayer of primary fetus cells was formed. Thereafter, the medium was removed and 1.5ml of aqueous trypsin solution of 0.05% (W/V) concentration were added per each plate, and the monolayer was treated enzymatically at 37° C for 15 minutes to peel the cells from the plate. The peeled cells were inoculated into 35 culture plates each 15cm in diameter containing 22.5ml of the same medium as described above at the rate of $2.25 \times 10^6$ cells per plate and were cultured for 48 hours under the same conditions. The medium in each plate was removed and the cells were washed three times with $PBS^{\ominus}$. Then, 22.5ml of an EM medium in which mouse serum albumin was dissolved (Fraction V, manufactured by Sigma Company) in a concentration of 1mg/ml were added to each plate. The plates were cultured in a carbon dioxide culture vessel at 37° C for 4 days whereby about 780ml of culture liquid containing protein in a concentration of 1.8mg/ml in the 35 plates was obtained. The culture liquid was ultrafiltered using a Diaflo-membrane, XM-100 (manufactured by Amicon Company) whereby a protein fraction of less than 100,000 molecular weight was obtained. The fraction was ultrafiltered using a Abcor-membrane, HFA-300 (manufactured by Bioengineering Company) whereby a protein fraction of greater than 50,000 molecular weight was obtained,. The fraction was lyophilized whereby about 600mg of white powdery therapeutic agent was obtained for animal experiment. The curing agent thus obtained was dissolved in $PBS^{\ominus}$ in a concentration of 10% and the acute toxicity was tested by intraperitonealy administering the curing agent to the test animals according to the Lichfield and Wilcoxon method (Journal of Pharmacology and Experimental Therapeutics, 90, 99, 1949). As a result, the therapeutic agent had an acute toxicity of 3,200 mg/Kg (LD50). Based on the acute toxicity so obtained, an experiment was run whereby the effective amount was determined as follows:

42 Six-week-old SL mice were injected with $1 \times 10^6$ M1 cells per mouse intraperitonealy. These mice were divided into 7 groups of 6 mice each. Continuously for 5 days from the next day, the 6 mice of the first group were injected with 0.5ml of sterilized physiological saline per day per each mouse intraperitonealy. The mice of the second group were injected with 0.5ml of 0.001% (by weight) aqueous solution of Mitomycin C which has hitherto been used as a curing agent for leukemia in the same animals (the administered amount has been recognized to be effective in animal experiments using leukemic cell L 1210). The mice of the third to seventh groups were injected with 0.5ml of aqueous solution of the above described therapeutic agent for animal experiment in an amount of 1/500, 1/250, 1/50, 1/5 and ⅓ times the acute toxicity dosage respectively. Each mouse was bred with water and feed and was given freely. The average survival in days of each group of mice was calculated and the index of each group for 100 of the average survival days of the control group was calculated therefrom whereby the degree of percentage of increased life span was determined. The results are shown in Table 5.

TABLE 5

| Test group No. | Kind of medicine administered | Amount administered (mg/kg body wt./day) | Average survival days | Degree of percentage of increased life span |
|---|---|---|---|---|
| 1 | Physiological saline (Control) | | 34 | 100 |
| 2 | Mitomycin C | 0.26(1/2OLD$_{50}$) | 37 | 109 |
| 3 | Therapeutic agent for animal experiment | 1070(1/3LD$_{50}$) | 37 | 109 |
| 4 | " | 640(1/5LD$_{50}$) | 49 | 144 |
| 5 | " | 64(1/50LD$_{50}$) | 50 | 147 |
| 6 | " | 12.8(1/250LD$_{50}$) | 49 | 144 |
| 7 | " | 6.4(1/500LD$_{50}$) | 39 | 115 |

As is evident from Table 5, the group which was administered Mitomycin C commercially available as a curing agent for leukemia exhibited an increased life span on a percentage basis in comparison to the control group by about 10%. In contrast, the groups which were administered the therapeutic agent for animal experiments obtained by the same method as the process of the present invention, particularly the 4th to 6th groups, exhibited a substantially increased percentage in life span. That is, the mice of the 4th to 6th groups exhibited a greater degree of percentage increase in life span than the 2nd group which was administered Mytomycin C by 1. 2 times. Therefore, the amount of therapeutic agent for the animal experiments administered to the mice of the 4th to 6th groups, i.e. 13 to 640mg/body weight 1Kg/day, is an effective administration amount.

Incidentally, in foregoing Tests 1 to 4, a therapeutic agent was prepared by inoculating precultured human amnion cells in a medium in a concentration of $1 \times 10^5$/ml and tested. However, when the therapeutic agent was prepared by inoculating the cells in other concentrations, the same results as in Tests 1 to 4 were obtained.

EXAMPLE 1

The amnion was cut from 3 placentas of women each of whom had delivered a child by Cesarean section and they were preserved in a sterilized Hanks liquid containing penicillin in a concentration of 0.3% (W/V) at 4° C for about 6 hours. The amnions were washed with sterilized PBS$^\ominus$ and twice with an Eagle MEM medium. The amnions were cut into about 5cm square pieces, were placed onto a plate, washed with sterilized EM medium three times and sliced aseptically by scissors. A 120ml amount of an aqueous solution of trypsin in a concentration of 0.25% (W/V) were added thereto and the amnion pieces were treated enzymatically at 37° C for about 30 minutes to isolate the cells. An EM medium containing 10% calf serum (Lot No. 5340, manufactured by MBL Company) was added to a trypsin digested suspension and then the suspension was passed through stainless steel Sieves of 80 mesh and 150 mesh in turn to remove the cell mass aseptically.

Human amnion cells in suspension were inoculated onto 30 plastic plates each 10cm in diameter and containing 10ml for sterilized EM medium to which was added 10% of calf serum in a concentration of $1 \times 10^7$ cells. The cells were cultured in a carbon dioxide culture vessel at 37° C for 10 days and the medium was replaced on every third day, whereby a monolayer of primary human amnion cells were obtained. After removing the medium, 1.5ml of 0.05% (W/V) aqueous trypsin solution was added thereto per plate and the monolayer was treated enzymatically at 37° C for 15 minutes to peel the cells from the plate. The peeled cells were inoculated on 35 culture plates 15cm in diameter containing 22.5ml of the same medium as described above at the rate of $2.25 \times 10^7$ cells each. The plates were cultured under the same conditions as described above for 3 days, and after removing the medium, the cultured monolayer was washed three times with PBS$^\ominus$.

Then, 22.5ml of an EM medium containing dissolved human serum albumin (Fraction V, manufactured by Sigma Company) in a concentration of 1mg per ml were added to each plate and the plates were cultured in a carbon dioxide culture vessel at 37° C for 4 days whereby about 780ml of a culture liquid containing protein in a concentration of 1.8mg/ml from 35 plates were obtained.

The cultured liquid was dialyzed against PBS$^\ominus$ to remove the medium components. Next, using a milipore filtration apparatus (manufactured by Japan Milipore Limited) provided with a 0.45μ membrane filter type TM-4 (manufactured by Toyo Filter Paper Company) which was sterilized in an autoclave at 120° C for 15 minutes, the above described culture liquid was filtered aseptically with a vacuum pump. Each 350ml sample of the aseptic filtrate was poured into a sterilized 500ml -glass tube for venous injection and sealed whereby two liquid therapeutic agents for instillation were obtained.

EXAMPLE 2

The secondary human amnion cells treated with trypsin and peeled by the same method as described in Example 1 were inoculated on a sterilized EM medium containing calf serum in a concentration of 10% thereby obtaining $8 \times 10^8$ cells per 8l of medium. The culture liquid was placed into 5 large cell culture vessels (manufactured by Sterilin Company) at the rate of each 1.6l per vessel, subsequently precultured under the same conditions as described in Example 1 for 3 days while rotating the cylinder at 2RPH and, after removing the medium, the preculture was washed three times with 400ml PBS$^\ominus$, 1.8l pf sterilized EM medium containing dissolved human serum albumin (Fraction V, manufactured by Sigma Company) were added in a concentration of 1mg/ml per culture vessel and the liquid medium was cultured in a carbon dioxide culture vessel at 37° C for 4 days whereby about 9l, in total, of a culture liquid containing protein in a concentration of 2.0mg/ml from 5 large cell culture vessels was obtained. The culture liquid was placed into a bag made of a dialysis membrane and was dialyzed in a metal vessel filled with 100l of PBS$^\ominus$ diluted by a factor of 50 times for 12 hours while cooling to 4° C and further dialyzed against 100l of PBS$^\ominus$ diluted by a factor of 8.7 times for 12 hours in the same manner. The dialyzed culture medium was then lyophilized whereby about 21g of a white powder was obtained. 20.6g of the powder were dissolved in 1,000ml of redistilled water and filtered aseptically in the same manner as described in Example 1 and thereafter partitioned and sealed aseptically into 20 ampules. Each ampule contained 50ml of a therapeutic agent for isotonic injection as a physiological saline solution.

EXAMPLE 3

The secondary human amnion cells obtained by the same method as described in Example 1 were further subcultured whereby the tertiary human amnion cells obtained were then cultured in 8 large cell culture vessels in the same manner as described in Example 2 to obtain about 14l of culture liquid. The culture liquid was dialyzed in the same manner as described in Example 2 with the exception that PBS$^\ominus$ solution was used which was diluted by a factor of 30 times and a PBS$^\ominus$ solution which was diluted by a factor of 8 times. The dialyzed culture medium so obtained was filtered aseptically in the same manner as described in Example 1 and further lyophilized aseptically according to the conventional method whereby about 33.2g of a white powder was obtained. 1.0g of the powder were partitioned aseptically into 33 ampules and sealed. When using the therapeutic agent, it is dissovled in 50ml of sterilized redistilled water.

EXAMPLE 4

About 14l of a culture liquid of human amnion cells obtained by the same method as described in Example 3 were ultra-filtered using Diaflomembrane, XM-100 (manufactured by Amicon Company) to fractionate a protein fraction of less than 100,000 molecular weight, the fraction was then ultra-filtered using an Abcor-membrane HFA-300 (manufactured by Bioengineering Company) and at the same time concentrated whereby about 300ml of a fraction of greater than 50,000 molecular weight was obtained. The fraction so obtained was filtered aseptically in the same manner as described in Example 1 and each 12ml of the filtrate was poured aseptically into 25 ampules. The filtrates were lyophilized aseptically and the ampules were sealed. Each ampule contained 640mg of a white powder. When using the therapeutic agent, it is dissolved in 20ml of sterilized PBS$^\ominus$.

What is claimed as new and desired to be secured by Letters Patent of the United States is:

1. A process for preparing a therapeutic agent, comprising the steps of: preculturing human amnion cells isolated from the human amnion by trypsinization or human amnion cells obtained by subculturing isolated amnion cells in a medium containing calf or bovine fetal serum at least 1 time for 1 to 5 days thereby forming a monolayer of cultured cells; separating said cultured cells from the culture medium; culturing said cells in a medium containing 0.5 to 20 mg of human serum albumin per 1ml of medium thereto for 3 to 6 days; dialyzing the culture medium against a diluted buffer or water; and filtering said dialyzed culture liquid through a bacterial filter thereby obtaining a germ-free liquid agent.

2. The process of claim 1, which further comprises: aseptically lypohilizing said liquid agent thereby obtaining a powdery therapeutic agent.

* * * * *